United States Patent
Shastri et al.

(10) Patent No.: US 12,396,623 B2
(45) Date of Patent: Aug. 26, 2025

(54) VISION SENSOR APPARATUS FOR MEDICAL DIAGNOSTIC APPLICATIONS

(71) Applicant: NSV, Inc., Allentown, PA (US)

(72) Inventors: Ankita Shastri, Bothell, WA (US); Rao Yelamarty, Allentown, PA (US); Soham Pathak, Allentown, PA (US); Sharvari Harsh Dalal, Munster, IN (US); Jeremy Lim, Emmaus, PA (US); Terry Ki Lim, Emmaus, PA (US); Neha Kumar, Macungie, PA (US)

(73) Assignee: NSV, INC., Allentown, PA (US)

( * ) Notice: Subject to any disclaimer, the term of this patent is extended or adjusted under 35 U.S.C. 154(b) by 407 days.

(21) Appl. No.: 17/908,305

(22) PCT Filed: Mar. 3, 2021

(86) PCT No.: PCT/US2021/020659
§ 371 (c)(1),
(2) Date: Aug. 31, 2022

(87) PCT Pub. No.: WO2021/178529
PCT Pub. Date: Sep. 10, 2021

(65) Prior Publication Data
US 2023/0116679 A1    Apr. 13, 2023

Related U.S. Application Data

(60) Provisional application No. 62/985,375, filed on Mar. 5, 2020.

(51) Int. Cl.
*A61B 1/00*    (2006.01)
*A61B 1/04*    (2006.01)
(Continued)

(52) U.S. Cl.
CPC ........ *A61B 1/00108* (2013.01); *A61B 1/0002* (2013.01); *A61B 1/04* (2013.01);
(Continued)

(58) Field of Classification Search
None
See application file for complete search history.

(56) References Cited

U.S. PATENT DOCUMENTS 5,840,012 A * 11/1998 Krauter ............. F16M 11/2014
600/102
6,088,612 A * 7/2000 Blair ........................ G06T 5/94
600/407
(Continued)

FOREIGN PATENT DOCUMENTS

WO    WO 2009051728    4/2009
WO    WO 2011047214    4/2011

*Primary Examiner* — John P Leubecker
(74) *Attorney, Agent, or Firm* — Millen, White, Zelano & Branigan P.C.; William F. Nixon

(57) ABSTRACT

A hand-held vision sensor apparatus comprises a plurality of light sources, control activation elements and an image sensing array, encased within a housing such that the control activation elements are disposed at a user-accessible location on the housing. The housing further includes a pair of exit apertures for emitting illumination directed toward a medical specimen and an entrance aperture for capturing reflected light from the medical specimen. The light sources are disposed in alignment with the pair of exit apertures, and the image sensing array is aligned with the entrance aperture. The control activation elements are utilized to energize the light sources and control the functioning of the image sensing array. A computer port may be included and used to communicate command controls to the light sources, image sensing array and control activation elements in a manner that allows for a remotely-located technician to communicate with the hand-held vision sensor.

21 Claims, 6 Drawing Sheets

(51) Int. Cl.
    *A61B 1/06*     (2006.01)
    *A61B 1/303*     (2006.01)

(52) U.S. Cl.
    CPC .......... *A61B 1/0646* (2013.01); *A61B 1/0684* (2013.01); *A61B 1/303* (2013.01)

(56) References Cited

U.S. PATENT DOCUMENTS

| | | | | |
|---|---|---|---|---|
| 6,101,408 | A * | 8/2000 | Craine | A61B 5/0086 |
| | | | | 382/128 |
| 6,260,994 | B1 * | 7/2001 | Matsumoto | A61B 1/0684 |
| | | | | 362/574 |
| 6,277,067 | B1 * | 8/2001 | Blair | A61B 1/0004 |
| | | | | 600/167 |
| 6,359,644 | B1 * | 3/2002 | Salvati | A61B 5/748 |
| | | | | 348/E7.085 |
| 6,818,903 | B2 * | 11/2004 | Schomacker | A61B 1/0607 |
| | | | | 250/461.2 |
| 8,786,689 | B1 * | 7/2014 | Liu | A61B 1/24 |
| | | | | 348/68 |
| 9,241,616 | B1 * | 1/2016 | Mortensen | A61B 1/0638 |
| 2003/0228553 | A1 * | 12/2003 | Mandelkern | A61B 1/0676 |
| | | | | 433/29 |
| 2005/0200707 | A1 | 9/2005 | Yogesan et al. | |
| 2006/0215406 | A1 * | 9/2006 | Thrailkill | A61B 1/0655 |
| | | | | 362/249.06 |
| 2007/0213590 | A1 * | 9/2007 | Squicciarini | A61B 1/00101 |
| | | | | 600/172 |
| 2008/0045791 | A1 * | 2/2008 | Gal | A61B 1/018 |
| | | | | 600/116 |
| 2008/0108869 | A1 * | 5/2008 | Sanders | A61B 1/00124 |
| | | | | 600/109 |
| 2010/0039700 | A1 * | 2/2010 | Ghosh | A61B 1/303 |
| | | | | 359/380 |
| 2011/0184272 | A1 * | 7/2011 | Zeng | A61B 17/42 |
| | | | | 600/407 |
| 2012/0237890 | A1 | 9/2012 | Liang et al. | |
| 2012/0320340 | A1 | 12/2012 | Coleman, III | |
| 2013/0034825 | A1 * | 2/2013 | Phillips | A61B 1/00183 |
| | | | | 433/29 |
| 2013/0148326 | A1 | 6/2013 | Goldfain | |
| 2013/0170024 | A1 * | 7/2013 | Teplitz | G02B 21/084 |
| | | | | 359/387 |
| 2014/0012137 | A1 | 1/2014 | Rosen | |
| 2014/0066727 | A1 | 3/2014 | Heine et al. | |
| 2014/0135581 | A1 * | 5/2014 | Wikstroem Shemer | A61B 1/0638 |
| | | | | 600/162 |
| 2015/0036311 | A1 | 2/2015 | Mullani | |
| 2015/0112411 | A1 * | 4/2015 | Beckman | A61N 5/0616 |
| | | | | 607/90 |
| 2016/0262604 | A1 * | 9/2016 | Greenstein | A61B 18/201 |
| 2016/0338590 | A1 * | 11/2016 | Sagalovich | A61B 1/00066 |
| 2017/0215700 | A1 * | 8/2017 | Lin | A61B 1/00042 |
| 2017/0265716 | A1 * | 9/2017 | Tago | A61B 1/00009 |
| 2018/0203338 | A1 | 7/2018 | Kawamura et al. | |
| 2019/0150725 | A1 * | 5/2019 | Ramanujam | A61B 1/015 |
| 2020/0315444 | A1 * | 10/2020 | Ramanujam | A61B 1/307 |
| 2021/0007596 | A1 * | 1/2021 | Landesman | A61B 1/00142 |
| 2021/0330180 | A1 * | 10/2021 | Koide | A61B 1/00011 |

\* cited by examiner

VISION SENSOR APPARATUS FOR MEDICAL DIAGNOSTIC APPLICATIONS

CROSS-REFERENCE TO RELATED APPLICATIONS

This application claims the benefit of U.S. Provisional Application No. 62/985,375, filed Mar. 5, 2020 and herein incorporated by reference.

TECHNICAL FIELD

The present invention relates to vision sensor apparatus for medical diagnostic applications and, more particularly, to an apparatus that utilizes multiple LEDs (selection controllable by the user) in a hand-held device that allows for the capture and storage of high quality images.

BACKGROUND OF THE INVENTION

There are several types of medical procedures that utilize image analysis of selected specimens to aid in the development of a proper diagnosis. Dermatoscopy, for example, may utilize an analysis of specific pigmentation characteristics in determining a diagnosis. Colposcopy is known to utilize analysis of vascular systems in evaluating a patient's condition. These are but two specific areas of the use of imaging analysis in the field of medicine.

A typical prior art optical colposcope comprises a binocular microscope with a built-in white light source and objective lens attached to a support mechanism. Various levels of magnification are often necessary to detect and identify certain vascular patterns indicative of the presence of more advanced pre-cancerous or cancerous lesions. During a colposcopic exam, acetic acid and iodine solutions are usually applied to the surface of the cervix to improve the visualization of abnormal areas. In some cases, different-colored filters are used to accentuate blood vessel patterns that cannot be easily seen by using regular white light.

Various prior art vision systems for these purposes are often bulky, sensitive to errors in positioning, and limited in the features available for controlling the quality of the images.

SUMMARY OF THE INVENTION

The needs remaining in the art are addressed by the present invention, which relates to vision sensor apparatus for medical diagnostic applications and, more particularly, to an apparatus that utilizes multiple LEDs (selection controllable by the user) in a hand-held device that allows a user to capture high quality images and videos.

In accordance with the principles of the present invention, a vision sensor apparatus is proposed that incorporates an illumination source with a controllable sensor configuration in a relatively small, hand-held device that includes user-friendly activation controls associated with features such as "zoom", "image capture" and "start/stop" (the last associated with video recording). The apparatus itself preferably includes a computer communication port that allows for the creation of a communication link to associated computer apparatus (e.g., for storage, data analytics related to captured images, transfer to cloud, etc.).

An exemplary embodiment of the present invention takes the form of a hand-held vision sensor apparatus comprising a plurality of light sources, control activation elements and an image sensing array, encased within a housing such that the control activation elements disposed at a user-accessible location on the outer surface of the housing. The housing further includes at least a pair of exit apertures for emitting illumination directed toward a medical specimen and an entrance aperture for capturing reflected light from the medical specimen. The plurality of light sources is disposed in at least a pair of spaced-apart locations within the housing so as to be aligned with the pair of apertures. The image sensing array is positioned in alignment with the receive aperture and the control activation elements are utilized to energize the plurality of light sources and control the functioning of the image sensing array. A computer port may be included and used to communicate command controls to the plurality of light sources, image sensing array and control activation elements in a manner that allows for a remotely-located technician to communicate with the hand-held vision sensor.

Other and further aspects and embodiments of the present invention will become apparent during the course of the following discussion and by reference to the accompanying drawings.

BRIEF DESCRIPTION OF THE DRAWINGS

Referring now to the drawings, where like numerals represent like parts in several views.

DETAILED DESCRIPTION

Figure 1:
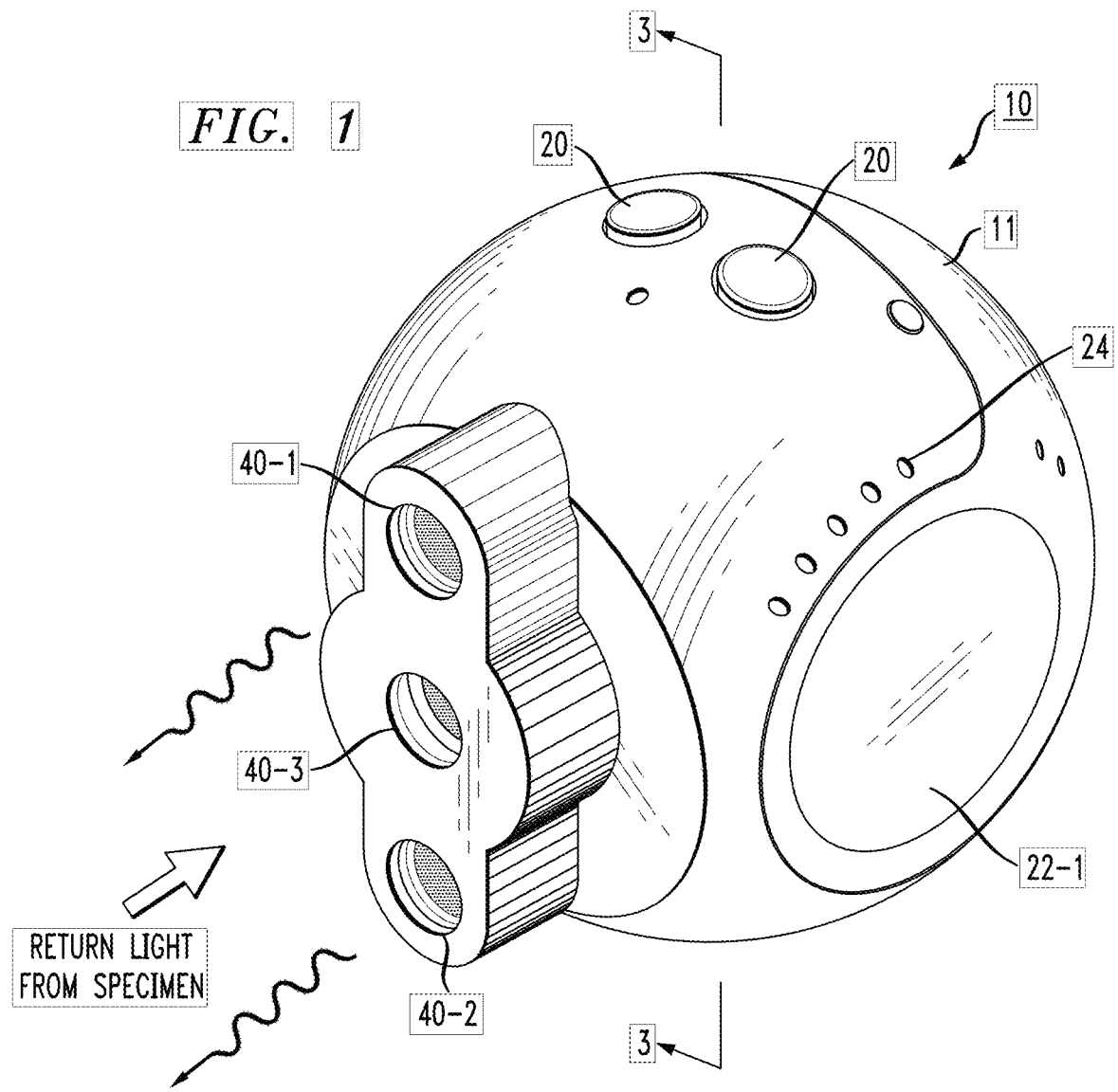
FIG. 1 is an isometric view of an exemplary hand-held vision sensor apparatus formed in accordance with the principles of the present invention.

FIG. 1 is an isometric view of an exemplary vision sensor apparatus 10 formed in accordance with one or more embodiments of the present invention. Apparatus 10 is shown as encased within a housing 11 that is relatively spherical in design, and is preferably formed of an injection-molded material (such as a plastic), with housing 11 formed to include the various openings and contours required for creating a workable device. Apparatus 10 is particularly configured to be used as a hand-held device, directing illumination toward a specimen and capturing return light for analysis and evaluation of a medical condition. In this embodiment of apparatus 10, the light beams for illumination exit from a pair of exit apertures 40-1 and 40-2, disposed as shown along a front face of housing 11. The return/reflected light enters apparatus 10 via an entrance aperture 40-3, shown in this case as positioned at a mid-point between exit apertures 40-1 and 40-2.

Apparatus 10 also includes a plurality of activation controls 20, located at a user-accessible position on housing 11.

In the particular embodiment shown in FIG. 1, activation controls 20 comprise a pair of buttons that are located at the top of spherical housing 11. The use of "buttons" as activation controls 20 is considered to be exemplary only and various other types of activation arrangements may be better suited for particular applications. For example, a capacitively-controlled touch pad may be used in some cases; alternatively, voice-activated control commands may be used. All of these alternatives, as well as many others, are considered to fall within the spirit and scope of the present invention.

A pair of grips 22 is preferably included on opposing sides of apparatus 10 (only grip 22-1 visible in the view of FIG. 1), where grips 22 are formed of a specific material/texture/elasticity, or the like, to allow for a user to easily grip hand-held apparatus 10 during a medical examination procedure. A plurality of vent holes 24 may be formed through the thickness of housing 11 to provide for thermal dissipation and heat flow control.

Figure 2:
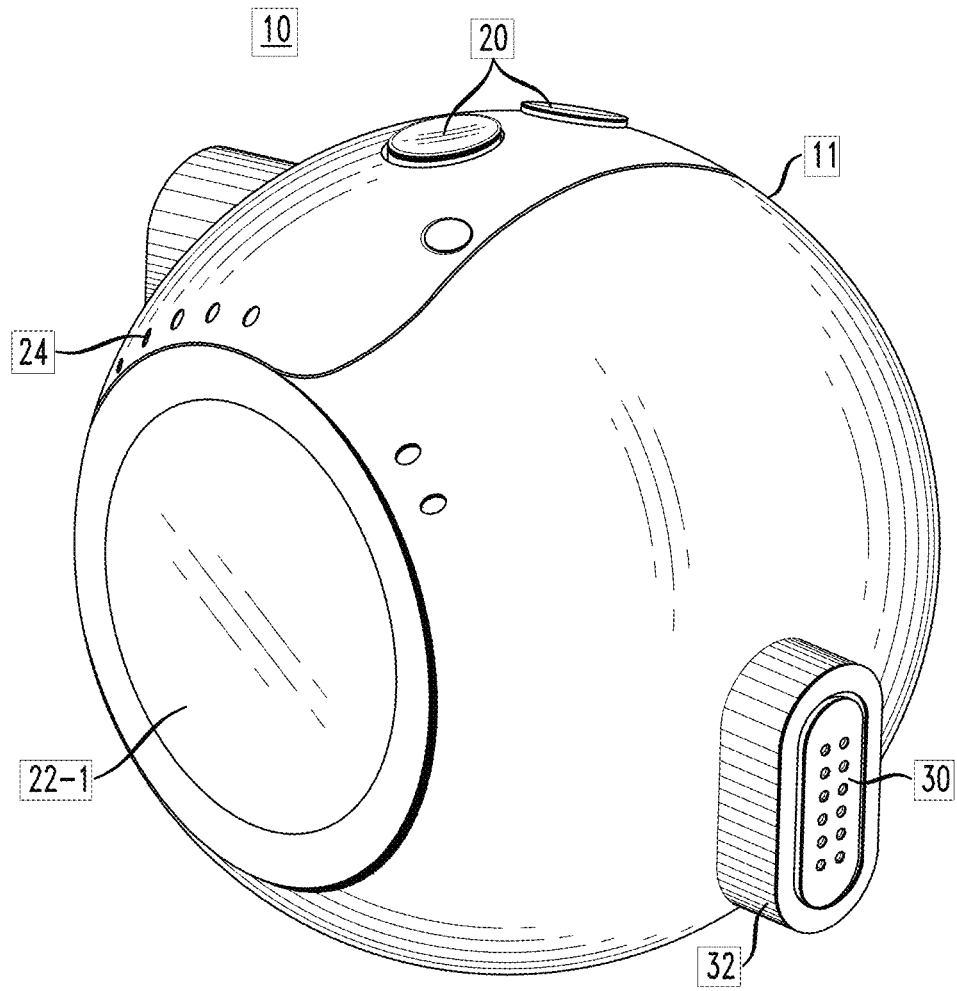
FIG. 2 is another isometric view of the vision sensor apparatus of FIG. 1, in this case viewing the hand-held apparatus from the rear.

FIG. 2 is another isometric view of apparatus 10, in this case showing the device from the rear so as to illustrate a computer port 30 (the example here being a special USB type C port; other types of ports may be used) that is used to connect vision sensor apparatus 10 to an associated computer, as well as provide a driver and power source. It is a particular feature and advantage of apparatus 10 as formed in accordance with the present invention that computer port 30 may be recessed within a connector housing protrusion 32 formed on housing 11 in the manner shown in FIG. 2. By virtue of using a recessed connection, the likelihood of accidental detachment of a connecting cable (not shown) from port 30 is minimized. Additionally, a USB type C cable with a magnetic coupler may be used that is attracted to the port magnetically to further prevent accidental detachment.

Figure 3:
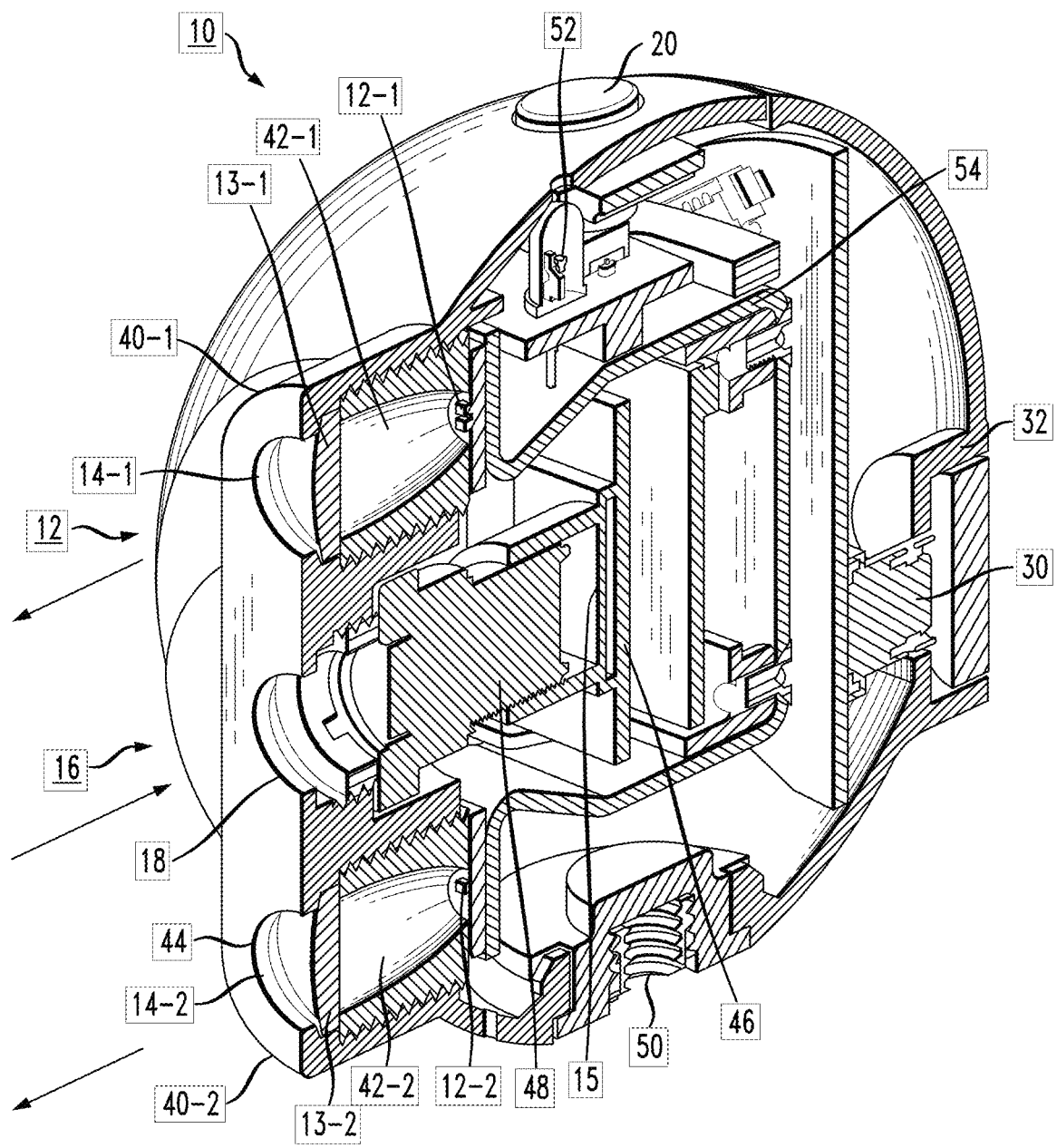
FIG. 3 is a cut-away isometric view of the inventive hand-held vision sensor apparatus, illustrating an exemplary positioning of vision components (for illumination of a specimen, and capture of reflected light from the specimen)
Figure 4:
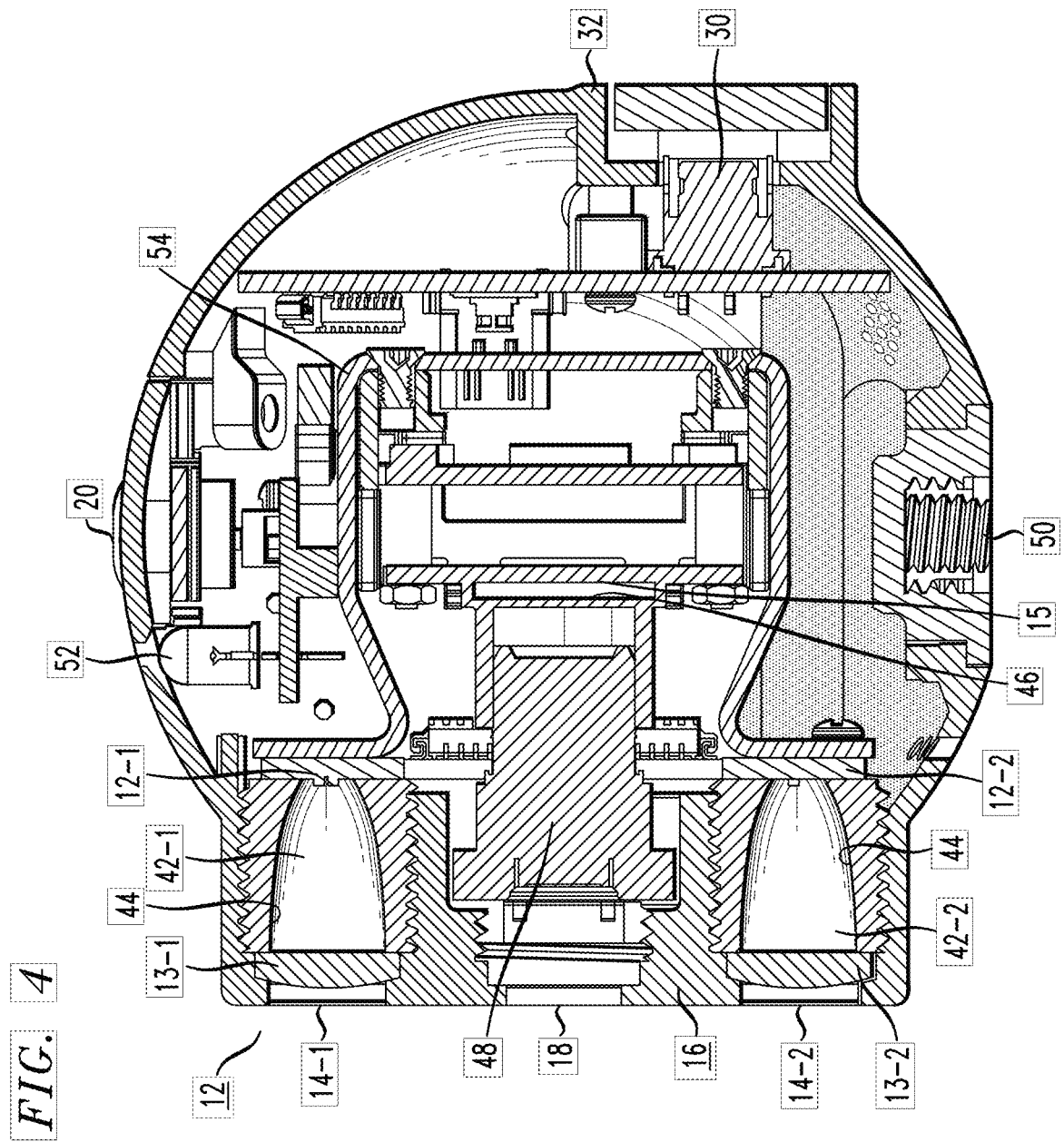
FIG. 4 is a two-dimensional cut-away view, similar to that of FIG. 3, illustrating in particular the position of individual optic elements along the exit and entrance paths.

FIG. 3 is a cut-away isometric view of apparatus 10, taken along line 3-3 of FIG. 1. FIG. 4 is a two-dimensional cut-away view of apparatus 10, also taken along line 3-3. Shown in both FIGS. 3 and 4 is a pair of light sources 12-1 and 12-2 that is utilized to produce the light beams used to illuminate a given specimen. Each light source 12 is positioned within housing 11 in optical alignment with a respective one of the exit apertures. That is, light source 12-1 is positioned in optical alignment with exit aperture 40-1 and light source 12-2 is positioned in optical alignment with exit aperture 40-2. Each light source 12 comprises one or more LED modules for providing light of different wavelengths (discussed below in association with FIG. 5) that is used to illuminate a given specimen under evaluation.

By including LEDs that emit at different wavelengths, a user may select a particular LED (i.e., a particular "color") for viewing, using an activation control element 20 to make the selection. Alternatively, the selection may be computer-controlled, with the commands received via computer port 30 and used to energize specific LEDs (and perhaps in a specific sequence) for a particular purpose. It is contemplated that LEDs in various wavelength ranges (e.g., visible, IR, UV, and the like) may be included, and configured to provide both broadband and narrowband imaging.

When used as an illumination source for a colposcope, the inventive LED-based source utilizes one or more LEDs that emit at specifically-defined wavelengths that are referenced as "green" and "blue". The green and blue wavelengths emitted by the LEDs is absorbed by the vessels, while being reflected by the surrounding tissue that lacks hemoglobin. This increases the contrast with which vessels appear in the image. The narrower the bandwidth of the blue and green light (i.e., bandwidths on the order of about 30 nm, or perhaps less) around hemoglobin's absorbance peaks, the greater is the contrast of the vessels in the resulting image. The high contrast between the tissues and vessels significantly improves the visualization of blood vessel patterns, where certain patterns are a known indicator of tissue abnormality. Reference is made to co-pending application serial number PCT/US20/26589, entitled "Medical Instrumentation Utilizing Narrowband Imaging", filed Apr. 3, 2020 and incorporated herein by reference, for a complete discussion of the details of using narrowband imaging of a medical specimen.

In some preferred embodiments, a pair of linear polarizers 14 may be used in combination with light sources 12 to ensure that light of only a defined, controlled polarization is emitted. As best shown in FIG. 4, a first linear polarizer 14-1 is positioned in alignment with first light source 12-1 and a second linear polarization 14-2 is positioned in alignment with second light source 12-2. It is important for linear polarizers 14-1 and 14-2 to be positioned along the same orientation (i.e., parallel to each other) so that both emitted beams exhibit the same polarization state. Here, linear polarizers 14-1 and 14-2 are disposed proximate to exit apertures 40-1 and 40-2, respectively.

Also shown in both FIGS. 3 and 4 is a pair of lenses 13 that is used in a conventional manner to control the shape of the beams exiting apparatus 10. Here, a first lens 13-1 is disposed between first linear polarizer 14-1 and first light source 12-1, with a second lens 13-1 disposed between second linear polarizer 14-2 and second light source 12-2. It is to be understood that lenses 13 may be used in certain embodiments that do not require the use of linear polarizers 14; their position with respect to light sources 12-1, 12-2 would remain essentially the same for these applications.

Additional focusing optics may be used along the path from light sources 12 to exit apertures 40-1 and 40-2, depending upon the application and the types of sources used for illumination. For example, an improvement in illumination efficiency (in terms of output illumination as a function of electrical drive applied to the LEDs) can be achieved by including beam redirection elements between light sources 12 and lenses 13. One exemplary type of beam redirection element is a parabolic diffuser, as shown in FIGS. 3 and 4.

As shown in these views, hand-held vison sensor apparatus 10 includes a pair of parabolic rings 42-1, 42-1 positioned between light sources 12-1, 12-2 and exit apertures 40-1, 40-2, respectively. In particular, parabolic rings 42 are positioned in the optical signal path between light sources 12 and lenses 13. The inner surface 44 of each parabolic ring 42 is formed of (or coated with) a material that functions to continuously diffuse and redirect any light emitted by sources 12 that does not immediately pass through their associated exit apertures, enabling more light to ultimately exit through apertures 40 and illuminate the specimen. Exemplary materials for coating inner surface 44 include, but are not limited to, chrome, silver, or barium sulfate. It is to be understood that the inclusion of parabolic diffusers is optional, and may not be required for some applications.

Also shown in FIGS. 3 and 4 is a sensor configuration 16 used to capture reflected light from the specimen under study, the reflected light entering apparatus 10 via entrance aperture 40-3. Sensor configuration 16 is used to create and store selected digital images and/or videos of the illuminated specimen for study and analysis. Sensor configuration 16 may comprise a charge-coupled device (CCD) or any other suitable type of active pixel sensor. For the medical diagnosis use of the inventive apparatus, a CMOS-based sensor may be preferred since they are known to provide the high quality image data needed for medical applications.

Similar to providing polarized illumination from light sources 12, a linear polarizer 18 may be disposed over entrance aperture 40-3 of sensor configuration 16 so as to receive light of only a certain polarization. Linear polarizer 18 is positioned to be orthogonal to linear polarizers 14, thus reducing glare and specular reflection that would otherwise interfere with the quality of the captured images and/or videos. When evaluating medical specimens, specular reflection has been found to negatively affect the appearance of images, particularly confounding medical images of tissue and hampering visualization of areas of interest. Since linear polarizer 18 is positioned to be orthogonal to polarizers 14, this orientation prevents reflected light that is polarized along the same angle as incident light (associated with specular reflection) from being detected by the sensor.

Sensor configuration 16 is particularly shown in FIGS. 3 and 4 as including an image capture device 46 (such as a CMOS-based device) and variable focus optics 48 (for example, a liquid lens) that can be used to enable "automatic focus" and control the quality of the captured image. In a preferred embodiment of apparatus 10, an activation control 20 may be used for these imaging purposes (under the control of the individual performing the procedure, or a connected computer system, or perhaps both). Additional magnifying optics may be disposed along this incoming optical signal path to image capture device 46, if necessary. In addition, an anti-reflective coating 15 may be included over image capture device 46 to reduce loss in the transmission of light to the sensor. In this way, while cross-polarizers inherently limit some amount of light that gets transmitted to the sensor, an anti-reflective coating on the lens over device 46 helps to ensure that light is not impeded from passing through to the sensor due to specular reflection from the lens itself.

Computer port 30 and connector housing protrusion 32 are also shown in the cut-away views of FIGS. 3 and 4, which clearly illustrate the recessed location of port 30 within protrusion 32 formed in housing 11. As mentioned above, the use of a recessed connection has been found to reduce the likelihood of accidental detachment of a connecting cable (not shown) from port 30. Additionally, a USB type C cable with a magnetic coupler may be used that is attracted to port 30 magnetically to further prevent accidental detachment.

Also shown in FIGS. 3 and 4 is a universal screw mount 50 that allows for apparatus 10 be attached to several different types of camera mounts, as typically found within different, worldwide medical facilities. Universal screw mount 50 is located at (and preferably flush with) the bottom surface of housing 11. An indicator LED 52 is also shown in the views of FIGS. 3 and 4, and is energized when a computer cable has been connected to port 30 (i.e., showing that apparatus 10 is now operating as a networked device). A metallic plate 54, disposed behind illumination sources 12, is advantageously used to transport heat away from the light sources (which is then directed out of apparatus 10 through vents 24).

Figure 5:
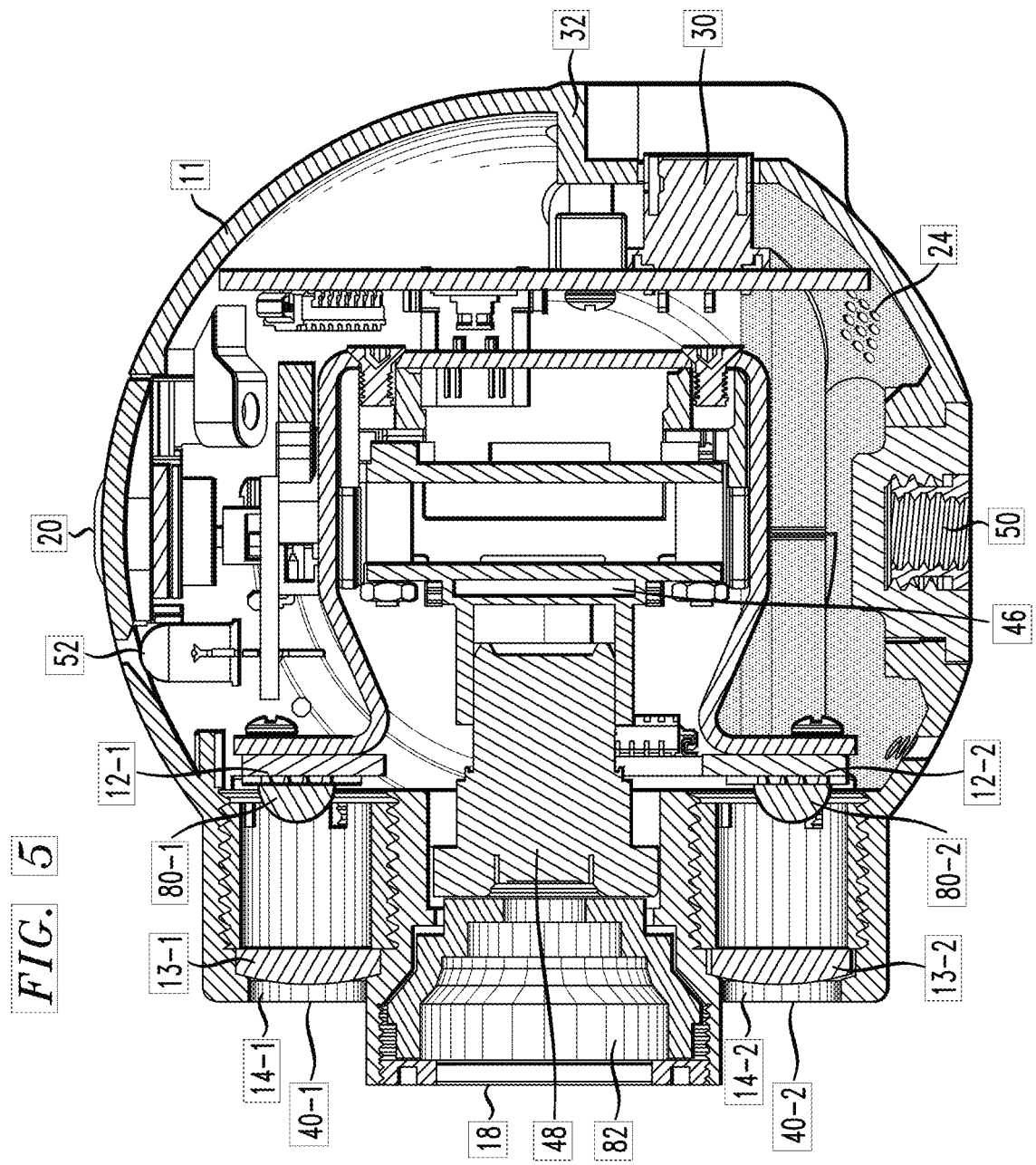
FIG. 5 is a two-dimensional cut-away view of an alternative embodiment of a vision sensor apparatus formed in accordance with the present invention.

FIG. 5 is a cut-away side view of another embodiment of the present invention, referred to as hand-held vision sensor apparatus 10A. In this embodiment, a pair of hemispherical lenses 80-1, 80-2 is used in combination with light sources 12-1, 12-2. As particularly shown in FIG. 5, hemispherical lenses 80 are used in place of parabolic rings 42 described above in association with the embodiment of FIGS. 3 and 4.

The inclusion of hemispherical lenses 80 allows for a higher proportion of light emitted from LEDs 12 to be directed through exit apertures 40-1, 40-2, which maintaining a relatively low intensity (preferred for various medical applications).

Also shown in apparatus 10A of FIG. 5 is a magnifying optic 82 disposed along the input path toward sensor configuration 16. For example, a telephoto lens may be used as optic 82, where in one exemplary embodiment a 2X telephoto lens was found advantageous in capturing detailed images of a specimen with high resolution of the features being analyzed. As another option, a passband filter may be positioned along the incoming signal path to minimize ambient "light noise" from entering sensor configuration 16 by passing only the wavelength range associated with LEDs 12.

Figure 6:
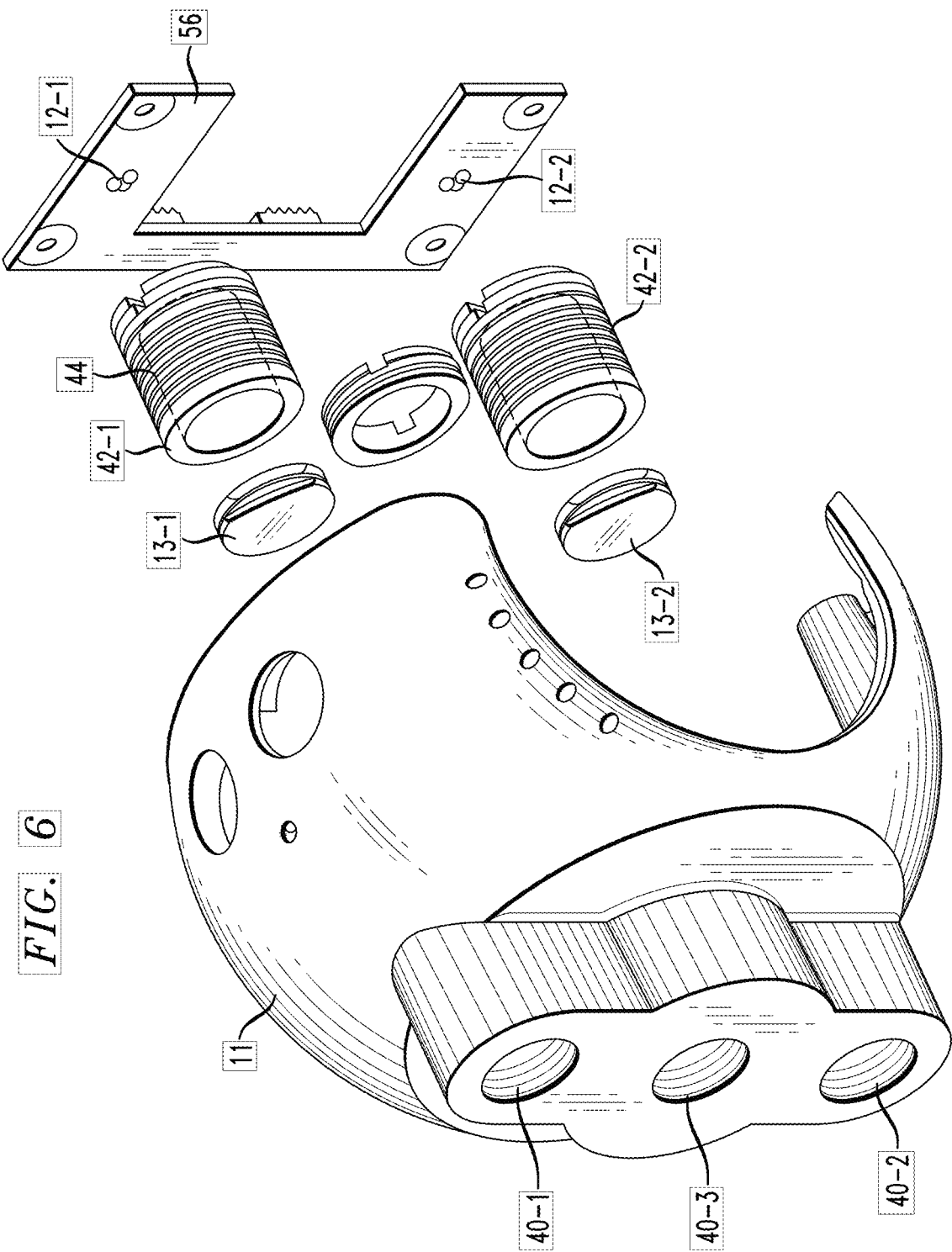
FIG. 6 is an exploded view of selected ones of the components used in the illumination portion of the inventive hand-held vision sensor apparatus.

FIG. 6 is an exploded view of light sources 12, illustrating the multiple groups of LEDs 12-1 and 12-2, as well as parabolic rings 42 (from the embodiment shown in FIGS. 2 and 3) and focusing lenses 13. Various other lensing arrangements (such as hemispherical lenses 80, among others) may be included along the signal path between LEDs 12 and emitting ports 40-1, 40-2.

In this particular embodiment, each LED group 12 is formed of a set of three separate LEDs, perhaps a "white light" visible LED and a pair of LEDs operating in the visible wavelength region (typically, "blue" and "green"). In various medical applications, it is also useful to utilize LEDs that emit a narrowband beam, as mentioned above, so that the vasculature appears more prominently in the image. In the case of colposcopy, the use of narrowband imaging with blue and green light allows the technician to better visualize the vasculature of the cervix. Also shown in FIG. 6 is a support plate 56, upon which LED groups 12 are mounted, while also used to provide the electrical connection to LEDs 12-1, 12-2.

While the above discussion of the apparatus of the present invention has been described in terms of a colposcopy application, it is to be understood that the inventive apparatus may be used for various other medical applications, such as imaging a portion of the skin's surface for dermatological reasons, or within a patient's mouth (such as when studying types of oral cancers).

A preferred embodiment of the present invention may attach optics in a releasable arrangement (for example, magnetic) so that the same apparatus can be used for either a colposcope or dermatoscope (or any other type of scopic tool used for medical imaging purposes).

It is to be understood that the above-described embodiments of the present invention represent only illustrative examples of the inventive principles being proposed, with variations and other embodiments likely to occur to those skilled in the art. Thus, the scope of the invention is considered to be limited only by claims appended hereto.

What is claimed is:

1. A vision sensor apparatus comprising:
  a housing, including a plurality of transmit apertures for emitting illumination directed toward a medical specimen and a receive aperture for capturing reflected light from the medical specimen;
  a plurality of light sources disposed in spaced-apart locations within the housing so as to be aligned with the plurality of transmit apertures, individual light sources of the plurality of light sources operating at wavelengths selected with respect to absorption or reflection of areas within the medical specimen;

focusing optics disposed between each light source of the plurality of light sources and its associated transmit aperture of the plurality of transmit apertures;

an image sensing array positioned in alignment with the receive aperture;

control activation elements disposed on the exterior of the housing and utilized to energize the plurality of light sources and control the functioning of the image sensing array; and a computer port formed on the exterior of the housing and coupled to the plurality of light sources, image sensing array and control activation elements in a manner that provides bidirectional communication between the vision sensor apparatus and an exterior computer system via a bus cable connection.

2. The vision sensor apparatus as defined in claim 1 wherein the plurality of light sources comprises LED modules aligned with the plurality of transmit apertures in a one-to-one relationship.

3. The vision sensor apparatus as defined in claim 2 wherein each LED module comprises a set of individual LEDs, each operating at a different wavelength.

4. The vision sensor apparatus as defined in claim 1, further comprising
a plurality of polarizers, each polarizer disposed in optical alignment with an associated light source, the plurality of polarizers aligned such that beams of like polarization are emitted by the vision sensor apparatus.

5. The vision sensor apparatus as defined in claim 4, further comprising a polarizer positioned along a light receiving path and disposed to exhibit a polarization orthogonal to the polarization of the plurality of polarizers to minimize glare in reflected illumination.

6. The vision sensor apparatus as defined in claim 4, wherein the plurality of polarizers comprises a plurality of linear polarizers.

7. The vision sensor apparatus as defined in claim 4, wherein the plurality of polarizers comprises a plurality of circular polarizers.

8. The vision sensor apparatus as defined in claim 1, further comprising
a plurality pair of lenses disposed in alignment with the plurality of transmit apertures.

9. The vision sensor apparatus as defined in claim 8, further comprising
at least one diffuser, each diffuser disposed between a selected paired combination of a lens and an emitting aperture of the plurality of lenses and the plurality of light sources, respectively, each diffuser configured to redirect spurious light emissions from the selected light sources back toward the selected lens.

10. The vision sensor apparatus as defined in claim 9 wherein an inner surface of each diffuser is coated with a light-diffusing material.

11. The vision sensor apparatus as defined in claim 10 wherein the light-diffusing material is selected from the group consisting of:
chrome, silver and barium sulfate.

12. The vision sensor apparatus as defined in claim 8, further comprising a plurality of hemispherical lenses, each hemispherical lens disposed over and adjacent to an associated light source of the plurality of light sources.

13. The vision sensor apparatus as defined in claim 1 wherein the image sensing array comprises a CMOS-based array.

14. The vision sensor apparatus as defined in claim 13 wherein the image sensing array further comprises an image storage element in communication with the CMOS-based array, providing storage for captured still image data and video image data.

15. The vision sensor apparatus as defined in claim 13 wherein the image sensing array further comprises a magnification optic disposed along a light receiving path at the input to the CMOS-based array.

16. The vision sensor apparatus as defined in claim 1 wherein the computer port is recessed within the housing.

17. The vision sensor apparatus as defined in claim 1 wherein the vision sensor apparatus further comprises a heat transfer plate, positioned as a mounting element for the plurality of light sources.

18. The vision sensor apparatus as defined in claim 1 wherein the housing includes a plurality of vent holes to aid in heat transfer away from the vision sensor apparatus.

19. The vision sensor apparatus as defined in claim 1 wherein the vision sensor apparatus further comprises a universal mounting component disposed on a centrally-located position on a bottom region of the housing.

20. The vision sensor apparatus as defined in claim 19 wherein the universal mounting component comprises a screw mount.

21. The vision sensor apparatus as defined in claim 19 wherein the universal mounting component comprises a magnetic mount.

* * * * *